US007930259B2

(12) United States Patent
Hashimoto et al.

(10) Patent No.: US 7,930,259 B2
(45) Date of Patent: Apr. 19, 2011

(54) APPARATUS FOR DETECTING VIBRATIONS OF A TEST OBJECT USING A COMPETITIVE LEARNING NEURAL NETWORK IN DETERMINING FREQUENCY CHARACTERISTICS GENERATED

(75) Inventors: Yoshihito Hashimoto, Amagasaki (JP); Hidekazu Himezawa, Kobe (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 709 days.

(21) Appl. No.: 12/000,590

(22) Filed: Dec. 14, 2007

(65) Prior Publication Data

US 2008/0144927 A1    Jun. 19, 2008

(30) Foreign Application Priority Data

Dec. 14, 2006    (JP) ................................. 2006-337373

(51) Int. Cl.
*G06E 1/00*            (2006.01)
(52) U.S. Cl. .............. 706/16; 324/633; 702/36; 702/75; 702/108; 73/577
(58) Field of Classification Search .............. 706/15–20, 706/45, 62; 324/71.1, 71.2, 76.21, 633–639; 702/34–36, 66, 75–77, 108–109; 73/32 R, 73/570, 645–648, 573–589
See application file for complete search history.

(56) References Cited

U.S. PATENT DOCUMENTS

| 5,419,197 | A | | 5/1995 | Ogi et al. |
| 5,589,635 | A | | 12/1996 | Baudrillard et al. |
| 5,904,215 | A | * | 5/1999 | Ikeda ............................. 180/169 |
| 6,198,843 | B1 | * | 3/2001 | Nakauchi et al. ............. 382/167 |
| 6,275,761 | B1 | * | 8/2001 | Ting ................................. 701/59 |
| 6,386,038 | B1 | | 5/2002 | Lewis, III et al. |
| 6,915,217 | B2 | * | 7/2005 | Springer et al. ................ 702/40 |
| 7,024,315 | B2 | * | 4/2006 | Giurgiutiu ...................... 702/33 |
| 7,290,450 | B2 | * | 11/2007 | Brown et al. ................... 73/579 |
| 7,539,549 | B1 | * | 5/2009 | Discenzo et al. .............. 700/28 |
| 7,778,947 | B2 | * | 8/2010 | Hashimoto ..................... 706/20 |

(Continued)

FOREIGN PATENT DOCUMENTS

JP            04-084754           3/1992

(Continued)

OTHER PUBLICATIONS

Neural Networks, http://web.archive.org/web/20061210150242/http://www.statsoft.com/textbook/stneunet.html, Dec. 10, 2006, downloaded Sep. 13, 2010.*

(Continued)

*Primary Examiner* — David R Vincent
(74) *Attorney, Agent, or Firm* — Bacon & Thomas, PLLC

(57) ABSTRACT

A nondestructive inspection apparatus includes a sensor unit for detecting vibrations transmitted through a test object from a vibration generator and a signal input unit for extracting a target signal from an electric signal outputted from the sensor unit. An amount of characteristics extracting unit is also included for extracting multiple frequency components from the test signal as an amount of characteristics. Further, a decision unit has a competitive learning neural network for determining whether the amount of the characteristics belongs to a category, wherein the competitive learning neural network has been trained by using training samples belong to the category representing an internal state of the test object, wherein distributions of membership degrees of the training samples are set in the decision unit.

4 Claims, 4 Drawing Sheets

U.S. PATENT DOCUMENTS

| | | | | |
|---|---|---|---|---|
| 2002/0161914 | A1* | 10/2002 | Belenki | 709/235 |
| 2004/0249520 | A1* | 12/2004 | Maine | 701/3 |
| 2005/0075846 | A1* | 4/2005 | Kim | 703/1 |
| 2006/0071666 | A1* | 4/2006 | Unsworth et al. | 324/522 |
| 2006/0112042 | A1* | 5/2006 | Platt et al. | 706/20 |
| 2006/0122810 | A1* | 6/2006 | Clarke et al. | 702/185 |

FOREIGN PATENT DOCUMENTS

| | | |
|---|---|---|
| JP | 04-124782 | 4/1992 |
| JP | 05-333079 | 12/1993 |
| JP | 07-311185 | 11/1995 |
| JP | 08-320875 | 12/1996 |
| JP | 2005-140707 | 6/2005 |
| JP | 2006-038478 | 2/2006 |

OTHER PUBLICATIONS

"Automated Sensory Inspection Based on Vibration and Acoustic Information", Ikeda Kazutaka et al., MEW Technical Report, Japan, Matsushita Electric Works, Ltd., Jun. 20, 2006, vol. 54/No. 2, pp. 42-48.

F.W. Margrave et al., "The use of neural networks in ultrasonic flaw detection", Measurement, Institute of Measurement and Control, vol. 25, No. 2, pp. 143-154, Mar. 1, 1999.

Zhao et al., "Ultrasound based glass fragments detection in glass containers filled with beverages using neural networks and short time Fourier transform", Food Research International, Elsevier Applied Science, vol. 39, No. 6, pp. 686-695, Jul. 1, 2006.

The European Search Report dated May 18, 2010.

* cited by examiner

APPARATUS FOR DETECTING VIBRATIONS OF A TEST OBJECT USING A COMPETITIVE LEARNING NEURAL NETWORK IN DETERMINING FREQUENCY CHARACTERISTICS GENERATED

FIELD OF THE INVENTION

The present invention relates to a nondestructive inspection apparatus for detecting a hole, a crack, a breakage, and the like generated in a test object without destroying same.

BACKGROUND OF THE INVENTION

There is known a testing method of inspecting whether a building wall is delaminated or peeled off by hearing sound with ears that is generated by hammering the wall. Moreover, there is widely known a method of hearing sound to check whether a fruit such as watermelon is ripe or not by tapping on same.

Such method of estimating an internal state of a test object by hitting the test object to impart vibrations thereto and hearing sound generated by the vibrations with ears, is widely applied in various fields.

There is also widely known a technology of ultrasonic diagnosis, which examines an internal state of a test object by emitting acoustic waves, e.g., ultrasonic waves, to the test object to impart therein acoustic vibrations and analyzing acoustic vibrations reflected from or transmitted through the inside of the test object.

However, in the method of estimating the internal state of the test object by hearing the sound generated when hitting the object, only an experienced person can tell the state by the sound so that only a limited number of persons can take part in the inspection. An apparatus such as an ultrasonic diagnosis instrument visualizes reflected waves from the inside of the test object so that the inner configuration of the test object can be understood. Since, however, the apparatus is configured to detect location information of the inside of the test object, the structure is complicated and expensive.

There is a technology capable of solving the various problems mentioned above by analyzing vibrations generated by hitting the test object using a neural network (see, for example, Japanese Patent Laid-open Application Nos. H7-311185 and 2006-38478).

The Japanese Patent Laid-open Application No. H7-311185 (referred to as 311185 patent hereinafter) discloses a technique, wherein decaying patterns and tone colors of sounds generated when hammering non-defective and defective objects are stored, and the sound generated when impacting a test object is compared with the stored sounds by the neural network to determine whether the test object is defective or not.

Moreover, Japanese Patent Laid-open Application No. 2006-38478 (referred to as 38478 patent hereinafter) discloses a technique that imparts vibrations to the test object without using the impulse hammering and determines whether an amount of characteristics of vibration waveform obtained from a test object corresponds to a non-defective or defective object by using a boundary learning neural network trained by amounts of characteristics of non-defective objects.

According to the 38478 patent, a pattern matching method employed in the boundary learning neural network, wherein an output pattern of group of output units (i.e. neurons of an output layer) corresponding to training samples is compared with a predetermined supervised pattern, then weight coefficients of the output units are compensated based on the difference between the output pattern and the supervised pattern and the neural network is trained by repeatedly compensating the weight coefficients after completing the training an output pattern of group of output units obtained by amounts of characteristics of a test object is compared with the trained output pattern. Further, the training samples are considered as samples having specific differences in the vicinity of an average value so that a distribution of the non-defective object is assumed as a normal distribution.

The 311185 patent discloses the technique of determining whether the test object is non-defective or not based on the hammering sound by using the neural network, but does not disclose a scheme of improving precision of the determination results obtained by using the neural network.

The 38478 patent determines whether the test object is non-defective or not by the pattern matching of output pattern using the neural network, so that the precision of the determination can be improved. However, the distribution of determinations for non-defectiveness or defectiveness is assumed to be the normal distribution, though cracks and breakage generated in test objects can be fairly random, therefore, if the whole non-defective test objects are assumed to have the normal distribution, there is a possibility that a category for the defective objects may be partially overlapped with the one for the non-defective objects.

In other words, if it is assumed that the distribution of the non-defective objects is the normal distribution, a region corresponding to the non-defective category is formed in a convex shape around an average value. Therefore, the technique disclosed in the 38478 patent cannot be employed if the above region corresponding to the non-defective category is partially formed in a concave shape. In other words, the precision determination for non-defectiveness or defectiveness may deteriorate depending upon the nature of a test object.

SUMMARY OF THE INVENTION

In view of the above, the present invention provides a nondestructive inspection apparatus for performing a test, which has been performed by human auditory sense conventionally, by using a competitive neural network to estimate an internal state of a test object without requiring skill and to increase estimation precision by determining a membership degree of amount of characteristics with respect to every neuron of an output layer.

In accordance with an aspect of the present invention, there is provided a nondestructive inspection apparatus including: a sensor unit for detecting vibrations transmitted through a test object from a vibration generator; a signal input unit for extracting a target signal from an electric signal outputted from the sensor unit; an amount of characteristics extracting unit for extracting multiple frequency components from the target signal as an amount of characteristics; and a decision unit having a competitive learning neural network for determining whether the amount of the characteristics belongs to a category, wherein the competitive learning neural network has been trained by using training samples belonging to the category representing an internal state of the test object.

Herein, distributions of membership degrees of the training samples are set in the decision unit, the distributions being set with respect to neurons excited by the training samples based on samples and weight vectors of the excited neurons.

Further, the decision unit determines that the amount of characteristics belongs to the category, if one of the excited neurons is excited by the amount of characteristics and the distance between the amount of characteristics and a weight vector each of one or more of the excited neurons, corresponds to a membership degree equal to or higher than a threshold determined by the distributions.

With such configuration, the frequency components of vibrations transmitted through the test object from the vibration generator are taken as the amount of characteristics, which is then classified by the competitive learning neural network. Thus, if the competitive learning neural network is properly trained, the test to distinguish sounds by human auditory perception can be operated by using the competitive neural network, so that the internal state of the test object can be estimated without requiring experiences.

The test object may be a steel material (e.g., an iron frame, a pipe, and a plate), and fruits (e.g., watermelon and melon), and it is possible to detect an anomaly such as a crack, a delamination, breakage, a hole, and the like therefrom.

Moreover, since a membership degree is set to each neuron of the output layer, zones corresponding to a normal category can be set to an arbitrary shape so that the precision of determination whether the test object is non-defective or defective can be improved even when a distribution of a non-defective object is not a normal distribution. In addition, since the competitive learning neural network is used, the structure is simple, and the neural network can be easily trained by collecting the training samples for every category and training the network based thereon.

It is preferable that the distributions of the membership degrees are Gaussian distributions each being defined by a mean and a variance, and wherein variances of the Gaussian distributions are determined by distances between the training samples and weight vectors of the excited neurons and means of the Gaussian distributions are weight vector of the excited neurons.

In this configuration, the distributions of the membership degrees of the category are assigned to respective neurons and set to Gaussian distributions. Therefore, the setting of the membership degree can be relatively easy even though the membership degrees are set to all neurons. Moreover, since a threshold can be set based on a variance or a sum of the membership degrees by using the Gaussian distributions, a method of setting the threshold as a determining reference can be formalized to be set automatically.

Alternatively, the vibration generator includes a hammer to transmit vibrations to the inside of the test object by impacting same.

In this configuration, the vibration generator includes the hammer to impart vibrations to the test object by hammering the test object. Thus, if there exists an anomaly inside the test object, the place where the anomaly exists can be estimated by varying the place where the hammer hits the test object. Further, since the vibration components generated by hammering the test object are employed as parameters of the amount of characteristics, a period of extracting the amount of characteristics can be easily determined, and the test can be always performed under the substantially identical conditions. In other words, reliability detecting the anomaly can be enhanced. Moreover, by considering the frequency components and the decaying characteristics thereof after impacting, the detailed internal state of the test object can be estimated by the impulse response.

Further, the vibration generator includes an acoustic wave generator to generate acoustic waves as the vibrations.

In this configuration, an acoustic wave generator generating acoustic waves is employed in the vibration generator 2. Therefore, the abnormal places can be detected without fail by continuously generating the acoustic waves and delivering same to the whole test object. Further, the impulse response or the step response can be monitored by changing the method of generating the acoustic waves. Therefore, the presence and/or the kind of anomaly can be estimated in detail by monitoring responses of differing kinds from locations where an anomaly is likely to exist.

BRIEF DESCRIPTION OF THE DRAWINGS

The objects and features of the present invention will become apparent from the following description of embodiments given in conjunction with the accompanying drawings, in which.

DETAILED DESCRIPTION OF THE EMBODIMENTS

Embodiments of the present invention will be described in detail with reference to the accompanying drawings which form a part hereof.

First Embodiment

Figure 1:
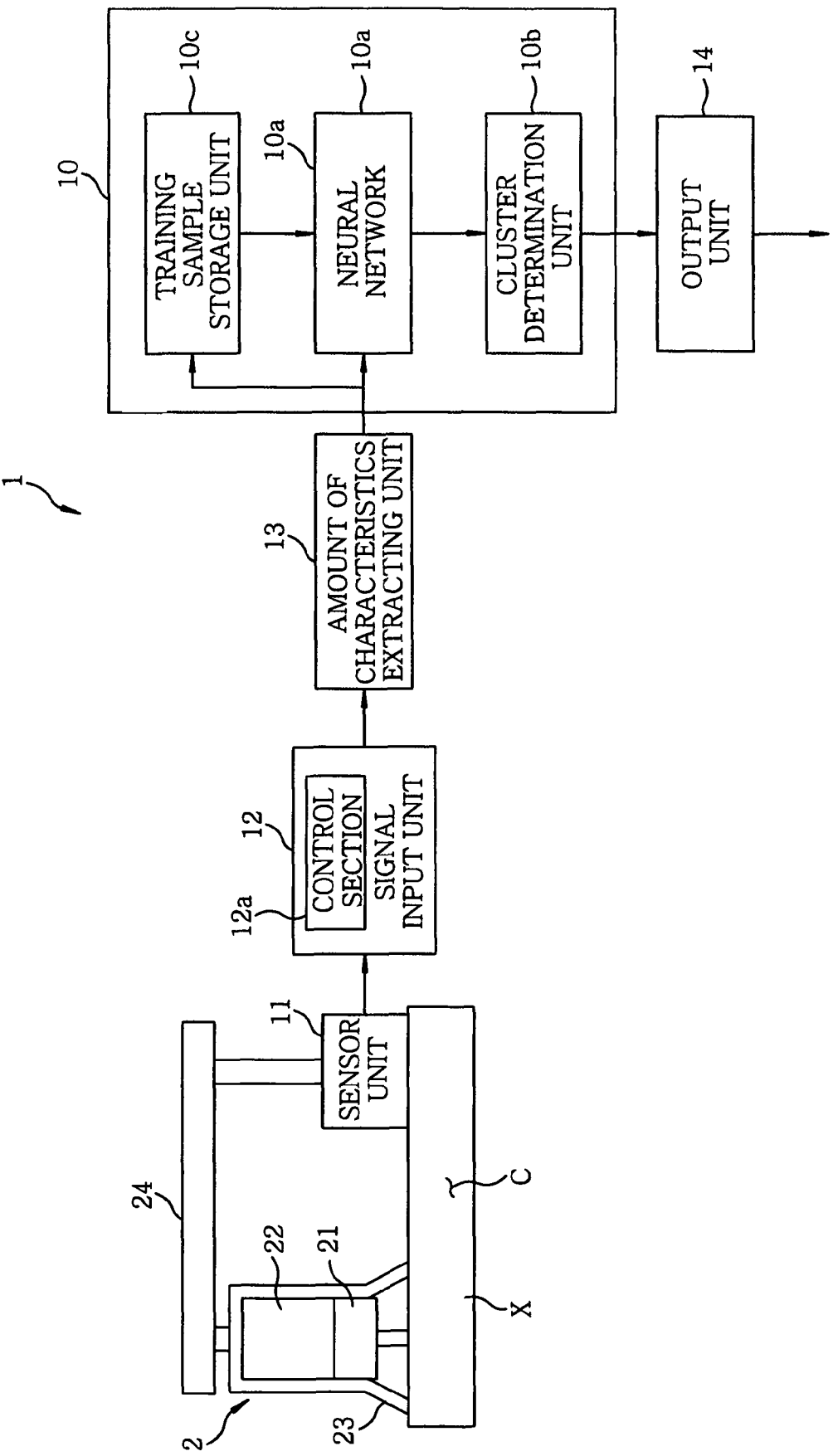
FIG. 1 shows a block diagram illustrating a nondestructive inspection apparatus in accordance with a first embodiment of the present invention.

In the present embodiment, a nondestructive inspection apparatus employing a vibration generator 2 to impart vibrations to a test object by hitting or tapping on same will now be described. As described above, although a test object such as a building, a steel material (e.g., an iron frame, a pipe, and a plate), and fruits (e.g., watermelon and melon) can be examined, in the present embodiment a steel material is assumed to be a test object X as shown in FIG. 1, and a crack C is generated in the test object X.

The vibration generator 2 includes a hammer 21 to hit the test object X and a driving unit 22 to move the hammer 21 back and forth. Preferably, the surface of the hammer 21 is covered with an elastic material to avoid making a scratch on the test object X when the test object X is hit to impart vibrations thereto. The driving unit 22 is configured to transmit an impact, which is generated e.g., by a driving force of an electromagnet (a solenoid to drive a plunger linearly), to the hammer 21.

As for the vibration generator 2, it may be considered that a steel hammer is used to hit the test object X by hand. Since, however, the impact force applied to the test object X may vary with every hit, detection precision can be deteriorated. Thus, it is preferred to use the vibration generator 2 to move the hammer 21 back and forth by the driving unit 22 so that uniform impact can be provided to the test object X. Moreover, the vibration generator 2 preferably includes legs 23 to contact the surface of the test object X to maintain a constant distance between the test object X and the hammer 21.

A nondestructive inspection apparatus 1 is provided to estimate an internal state of the test object X by inspecting vibrations transmitted to the test object X by the hitting of the vibration generator 2. The nondestructive inspection apparatus 1 includes a sensor unit 11 for detecting the vibrations transmitted to the test object X from the vibration generator 2.

The sensor is, e.g., a vibration sensor employing an acceleration pickup and is used to detect the vibrations of the test object X by contacting therewith. It is also possible to use a microphone as the sensor unit 11 to detect vibrations (sound of the vibrations) without contacting with the test object X.

It is preferable to maintain constant the positional relationship between the vibration generator 2 and the sensor unit 11 (particularly, the distance therebetween on the surface of the test object X). However, it is possible that a position of the vibration generator 2 is changed with respect to the test object X while a position of the sensor unit 11 is fixed with respect to the test object X. On the contrary, it is also possible to fix the position of the vibration generator 2 with respect to the test object X while changing the position of the sensor unit 11 with respect to the test object X. Although the positional relationship between the sensor unit 11 and the vibration generator 2 is changed in either case, it is possible to detect whether the inside of the test object X is abnormal or not.

Maintaining the constant positional relationship between the vibration generator 2 and the sensor unit 11, the vibration generator 2 and the sensor unit 11 can be achieved by coupling by an arm 24. In this case, at least one of the vibration generator 2 and the sensor unit 11 is attached to the arm 24 such that the position of the at least one can be adjusted with respect to the arm 24 to enable both of the vibration generator 2 and the sensor unit 11 to contact with the test object X. For example, both of the vibration generator 2 and the sensor unit 11 can be attached to be movable back and forth with respect to the arm 24 and can be biased by springs to contact with the test object X. In such case, the vibration generator 2 and the sensor unit 11 can contact with the test object X regardless of the surface shape thereto.

The nondestructive inspection apparatus 1 employs a neural network 10a to classify categories associated with characteristics of electric signals outputted from the sensor unit 11. The neural network 10a will be described in detail later. The electric signals being used to classify the categories are those outputted from the sensor unit 11 only while vibrations, transmitted to the test object X by hitting, continue after hitting the test object X by the vibration generator 2. The electric signals outputted from the sensor unit 11 during such period are inputted into a signal input unit 12, which extracts target signals therefrom.

Figure 2:
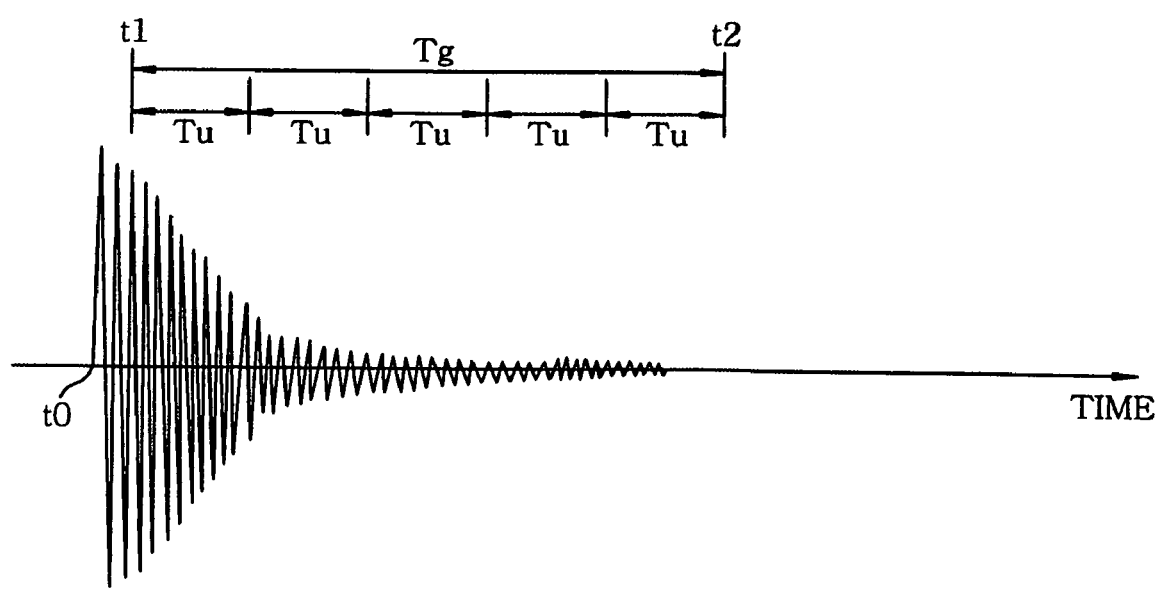
FIG. 2 is a view illustrating an operation of the nondestructive inspection apparatus shown in FIG. 1.

In the signal input unit 12, as shown in FIG. 2, electric signals within a gate period Tg set after hitting the test object X by the vibration generator 2 are selected among the electric signals outputted from the sensor unit 11. The gate period Tg is divided into a plurality of unit periods Tu so that an electric signal within each unit period Tu are used as a target signal St. A time period (t1−t0) from time t0 when the vibration generator 2 hits the test object X to time t1 when the gate period Tg is started and a time period (t2−t1) of the gate period Tg are properly adjusted. Also, the number of the unit periods Tu in the gate period Tg is appropriately adjusted. Such adjustment is performed by a control section 12a provided in the signal input unit 12.

For example, if the test object X is a steel pipe where reverberation after hitting continues for a long time, the gate period Tg is set to be longer. Further, if the distance between the vibration generator 2 and the sensor unit 11 is big, the time period (t1−t0) is set to be large. The reason why the gate period Tg is not started simultaneously with the hitting is to prevent noises, which generated from the vibration generator 2 when hitting the test object X, from being detected as the target signals.

The signal input unit 12 has an A/D converter for converting the electric signals outputted from the sensor unit 11 into digital signals and a buffer for storing the electric signals obtained during the gate period Tg and converted into the digital signals. The signal input unit 12 operates a processing of dividing electric signals into the target signals St each for every unit period Tu, with respect to the electric signals stored in the buffer. Further, the signal input unit 12 performs a frequency bandwidth limitation or the like in order to reduce noises when necessary.

The target signals St produced by the signal input unit 12 are inputted into an amount of characteristics extracting unit 13, which extracts frequency components from every target signal St as a part of the amount of characteristics. Moreover, in order to detect an impulse response of the test object X through the use of decaying characteristics of vibrations after the hitting, the amount of characteristics extracting unit 13 obtains an effective value (e.g., root mean square) of power for every target signal St to thereby extract a time series of effective values during the gate period Tg as a part of the amount of characteristics. If there exist, e.g., cracks or holes in the test object X, they change transmission paths of vibrations and thus the decaying characteristic of vibrations are affected. Therefore, the internal state of the test object X can be estimated in detail by detecting the frequency components and the impulse response.

The amount of characteristics extracting units 13 may use FFT (Fast Fourier Transform) in order to extract the frequency components. Which frequency is used in the amount of characteristics can be properly determined depending on the nature of the test object to be evaluated. In general, if the order is high, the FFT is advantageous compared to the linear regression since the former can obtain spectra faster than the latter.

As described above, the amount of characteristics having, e.g., the time series of powers in the gate period Tg and the frequency components for every target signal St as parameters thereof is inputted into a decision unit 10, so that the categories of the amount of characteristics are classified. The decision unit 10 uses an unsupervised competitive learning neural network 10a (hereinafter, simply referred to as a neural network if not otherwise necessary) to classify the categories of the amount of characteristics. A supervised back-propagation neural network can be also used as the neural network, but the unsupervised competitive learning neural network is more appropriate for this purpose since the unsupervised competitive learning neural network have simpler configuration than the supervised back-propagation type, and training of the unsupervised competitive learning neural network can be made only once by using training samples of every category, or can be enhanced further by performing additional training.

Figure 3:
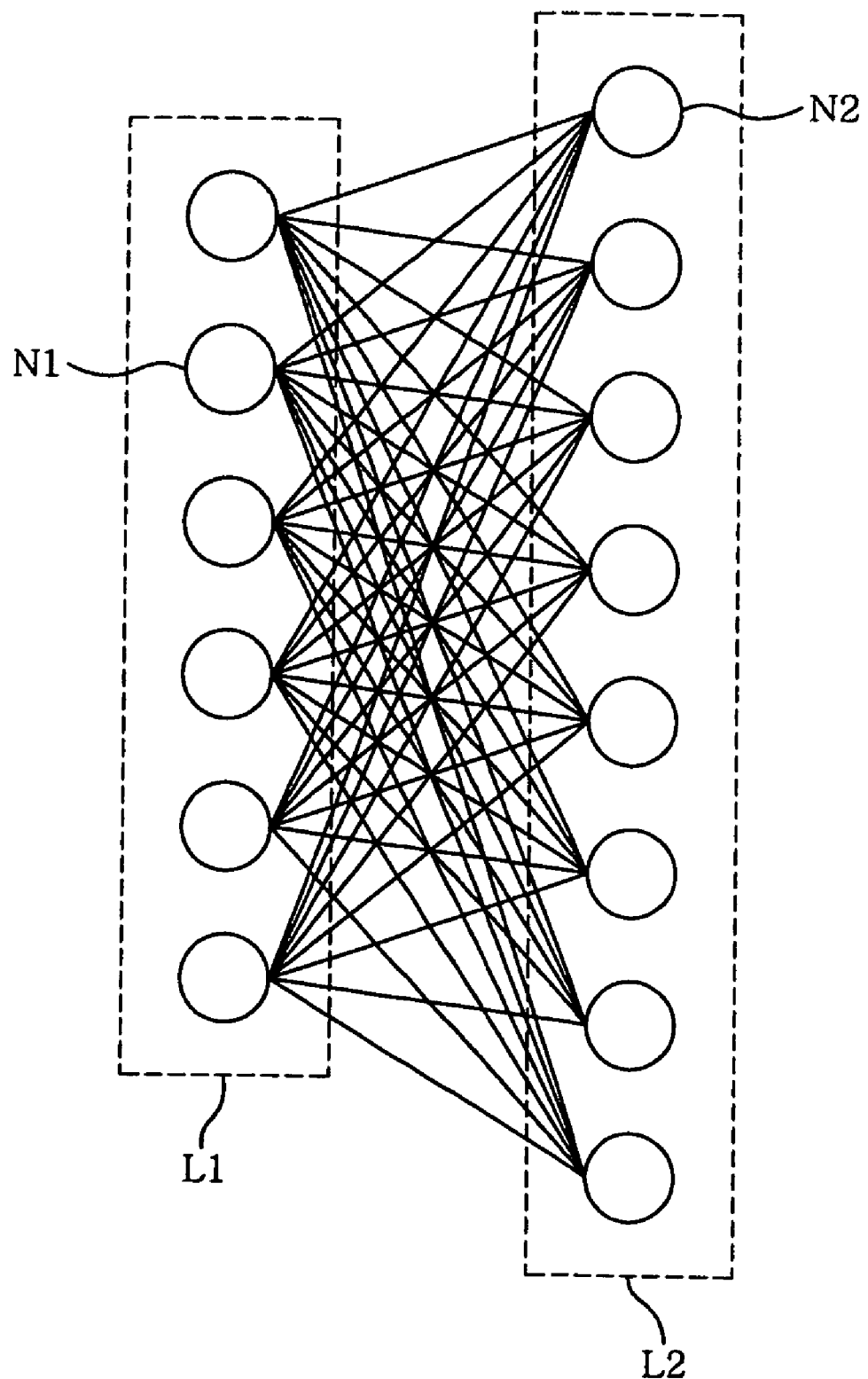
FIG. 3 illustrates a schematic configuration of a neural network used in the nondestructive inspection apparatus shown in FIG. 1.

As shown in FIG. 3, the neural network 10a has two layers, i.e., an input layer L1 and an output layer L2, and is configured such that every neuron N2 of the output layer L2 is connected to all neurons N1 of the input layer L1. The neural network 10a may be executed by an application program running at a sequential processing type computer, but a dedicated neuro-computer may be used.

The neural network 10a has two modes of operations, i.e., a training mode and a checking mode. After learning through proper training samples in the training mode, an amount of characteristics (check data) formed of a plurality of parameters generated from an actual target signal is classified into a category in the checking mode.

A coupling degree (weight coefficients) between the neurons N1 of the input layer L1 and the neurons N2 of the output layer L2 is variable.

In the training mode, the neural network 10a is trained by inputting training samples to the neural network 10a so that respective weight coefficients between the neurons N1 of the input layer L1 and the neurons N2 of the output layer L2 are decided. In other words, every neuron N2 of the output layer L2 is assigned with a weight vector having weight coefficients associated with all the neurons N1 of the input layer L1 as elements of the weight vector. Therefore, the weight vector has the same number of elements as the number of neurons N1 in the input layer L1, and the number of parameters of the amount of characteristics inputted to the input layer L1 is equal to the number of the elements of the weight vector.

Meanwhile, in the checking mode, when check data whose category needs to be decided is given to the input layer L1 of the neural network 10a, a neuron N2 having the shortest distance between the its weight vector and the check data is excited among the neurons N2 of the output layer 12. If categories are assigned to the neurons N2 of the output layer L2 in the training mode, a category of the check data can be recognized by a category of a location of the excited neuron N2.

The neurons N2 of the output layer L2 are associated with zones of respective a two-dimensional cluster determination unit 10b having, e.g., 6*6 zones in one-to-one correspondence. Therefore, if categories of the training samples are associated with the zones of the cluster determination unit 10b, a category corresponding to a neuron N2 excited by check data can be recognized by the cluster determination unit 10b. Thus, the cluster determination unit 10b can function as an output unit for outputting a classified result by the neural network 10a. Here, the cluster determination unit 10b may be visualized by using a map.

When associating categories with each of the zones of the cluster determination unit 10b (actually each of the neurons N2 of the output layer L2), trained neural network 10a is operated in the reverse direction from the output layer L2 to the input layer L1 to estimate data assigned to the input layer L1 for every neuron N2 of the output layer L2. A category of a training sample having the shortest distance with respect to the estimated data is used as a category of a corresponding neuron N2 in the output layer L2.

In other words, a category of a training sample having the shortest distance with respect to a weight vector of a neuron N2 is used for a category of the corresponding neuron N2 of the output layer L2. As a result, the categories of the training samples are reflected to the categories of the neurons N2 of the output layer L2.

A large number of training samples (for example, 150 samples) are employed to each of the categories so that categories having similar attributes are arranged close together in the cluster determination unit 10b. In other words, the neurons N2, excited among the neurons N2 of the output layer L2 in response to training samples belonging to a like category, form a cluster formed of a group of neurons N2 residing close together in the cluster determination unit 10b.

The cluster determination unit 10b is originally the one in which cluster is formed in association with categories after training, but in the present embodiment even the one before training is also called the cluster determination unit 10b so that it is not distinguished in this context. The training samples given to the neural networks 10a operating in the training mode are stored in respective training sample storage 10c, and retrieved therefrom to be used in the respective neural network 10a when necessary.

The training samples are collected and stored in the training sample storage 10c prior to the training mode. As for a training sample, an amount of characteristics obtained from a test object X predetermined as normal is used. In the neural network 10a of the present embodiment, the categories are set such that all categories other than normal categories are determined as abnormal. Thus, when collecting the training samples, amounts of characteristics obtained from test objects X predetermined as normal while changing various conditions such as temperature, humidity, or hitting points and sizes of the test object X, are stored as the training samples belonging to the normal categories in the training sample storage 10c.

In the present embodiment, after setting the categories in the neural network 10a by using the training samples, a Gaussian function is assigned to every neuron N2 of the output layer L2 of the neural network 10a before inputting an actual amount of characteristics obtained from the test object X to the neural network 10a. The following formula is used for the Gaussian function. In the following formula, the bracketed characters represent vectors.

$$y = \exp(-\|[x] - [m]\|^2 / 2\sigma^2)$$

where [m] is a mean and $\sigma^2$ is variance.

The weight vector of each neuron N2 of the trained neural network 10a is used as the mean [m] in the above formula for each neuron N2. The vector [x] in the above formula is an amount of characteristics inputted to the neural network 10a. ∥[x]−[m]∥ is the distance between the amount of characteristics [x] and the mean [m] (that is, the weight vector of the neuron N2. y is an output value obtained when imputing the amount of characteristics [x] into the Gaussian function of the above formula.

According to the formula, the output value y increases as the amount of characteristics [x] is closer to the mean [m], so that the output value y is maximized to "1" when the amount of characteristics [x] is equal to the mean [m]. This output value y is used as a membership degree. That is, a range of the output value y is from "0" to "1" wherein the membership degree is higher when the value is greater (when closer to "1").

Meanwhile, in order to calculate the variance $\sigma^2$, the training samples are inputted again to the trained neural network 10a to calculate distances between the amounts of characteristics (i.e., training samples) and the weight vectors [m] of the neurons N2. It is preferable to make lists of distances by giving all the training samples of a same category to the neural network 10a and employing maximum values of the distances calculated with respect to the neurons N2 as the variances.

For instance, a maximum of distances between a neuron N2 and training samples which have excited that neuron N2 can be used as the variance $\sigma^2$ for the Gaussian function of that neuron N2, alternatively, a maximum of the distances between all the training samples of a category and each neuron N2 belongs to that category can be used as the variance $\sigma^2$ for that neuron N2.

By doing so, the Gaussian function can be set to every neuron N2 corresponding to category of the training samples. The Gaussian function is not set to the neurons N2 belonging to other categories. That is, Gaussian function for neurons N2 corresponding to one category are set by training samples belonging to that category and these for another category are set by training samples belonging to the another category. By assigning the Gaussian function to every neuron N2 of the output layer L2 of the neural network 10a, a membership degree can be obtained by applying the distance between the amount of characteristics and the weight vector to the Gaussian function.

Specifically, after setting the Gaussian function for each neuron N2, the amount of characteristics [x] obtained from the test object X is inputted, and the distance between the amount of characteristics [x] and the weight vector (i.e., a mean [m]) of a neuron N2 excited thereby from the neural network 10a is substituted into the Gaussian function of the excited neuron N2, thereby obtaining the output value y of the Gaussian function for the excited neuron N2, corresponding to a category.

Since the output value y is the membership degree of the amount of characteristics with respect to the category corresponding to the excited neuron N2 as described above, it can be determined whether the amount of characteristics belongs to the category or not by setting a threshold with respect to the membership degree.

The threshold of membership degree for each neuron N2, for example, to have a value as large as three times the variance thereof or to be a product of a proper coefficient and a sum of the output values y of excited neurons N2 of the output layer L2 when training samples of a category are assigned to the neural network 10a after setting the Gaussian functions. The membership degree of an amount of characteristics can be determined in terms of only the neuron N2 excited by the amount of characteristics, as described above. Alternatively, a mean or a maximum of the output values y obtained from the Gauss functions of all the neurons N2 belonging to the category of the neuron N2 excited by an amount of characteristics can be used as the membership degree of that amount of characteristics.

As described above, the frequency components of the respective target signals St and the time series of effective value in the gate period Tg are used as parameters of an amount of characteristics, and one set of amount of characteristics can be obtained whenever the test object X is hit by vibration generator 2. Hereinafter, the one set of the amount of characteristics thus obtained is referred to as a data set. Data sets are collected under various conditions with respect to the normal test objects X, and multiple groups of data sets are stored in the training sample storage 10c. The frequency characteristics and a set of the time series of the effective values of powers for the unit periods Tu in the gate period Tg are used as the data set in the above example. However, only the frequency characteristics from parts of the unit period Tu in the gate period Tg or only the time series of powers in the gate period Tg may be used as the data sets.

When the neural network 10a is operating in the training mode, the weight coefficients associated with the neurons N2 of the output layer L2 is set by continuously assigning the data sets stored in the training sample storage 10c to the neural network 10a. Since the weight coefficients are gradually convergent by assigning a plurality of data sets to the neural network 10a, the weight coefficients after assigning the proper number of data sets is regarded as weight coefficients corresponding to the normal test object X.

After the training mode, all data sets stored in the training sample storage 10a are assigned to the neural network 10a again so that the neurons N2 of the output layer L2 excited by the training samples are considered as neurons N2 belonging to the categories of the normal test object X in the checking mode. Here, since there is a difference between the respective data sets of the training samples, each data set of the training samples in a normal category excites more than one neuron N2.

In the cluster determination unit 10b, zones corresponding to the neurons N2 excited by the data sets of the training samples become zones corresponding to the normal categories. The neurons N2 belonging to a same category are positioned to each other to form a cluster in the cluster determination unit 10b. Herein, since only the normal categories are associated with the zones of the cluster determination units 10b, the aforementioned operating in the reverse direction after training to set categories can be omitted.

After setting the normal zones in the cluster determination unit 10b, amounts of characteristics obtained from the test object X are inputted to the neural network 10a in the checking mode so that categories are classified with respect to the amounts of characteristics. Here, if a neuron N2 belonging to the categories of the normal test object X is not excited by the amount of characteristics obtained from the test object X (i.e., if the excited neuron N2 does not belong to the normal categories in the cluster determination unit 10b), the corresponding amount of characteristics is considered as abnormal.

The category determination result obtained by the cluster determination unit 10b is outputted to an output unit 14. When the amount of characteristics obtained from the test object X is abnormal, the output unit 14 may be configured to control a proper alarm device to issue alarm when necessary.

As described above, in the present embodiment, the test object X is impacted by the hammer 21 disposed in the vibration generator 2, and the sensor unit 11 detects the vibration transmitted through the test object X. Thereafter, the amount of characteristics thereof is classified by the neural network 10a to determine whether the test object X is normal or abnormal. Thus, it is possible to reliably detect whether the test object X is normal or not by the vibration imparted by hitting. Moreover, since the vibration generator 2 is implemented by a mechanical device, the training samples and the check data of the neural network 10a are obtained under the substantially identical conditions, so that reliability of the determination result can be enhanced.

In the present embodiment, the training of the neural network 10a is carried out by using training samples, obtained from normal test objects X only while changing conditions when hitting the normal test objects X. Thus, the clusters corresponding to the normal categories can be formed, facilitating the training of the neural network. However, the above-described embodiment detects only whether a test object is normal or not without identifying the nature of the anomaly. Therefore, judgment for the kind or state of the anomaly inside the test object X cannot be made; and thus an additional device is required.

If it is necessary to classify a kind of anomaly, the amounts of characteristics obtained from a test object X having an identified anomaly of the kind may be used as training samples. If the neural network 10a is trained by using the anomaly as one category, the kind of the anomaly can be used as a category of the cluster determination unit 10b. In this case, trained neural networks 10a needs to be operated in the reverse direction from the output layer L2 to the input layer L1 to estimate data assigned to the input layer L1 for every neuron N2 of the output layer L2 as described above. A category of a training sample having the shortest distance with respect to the estimated data is used as a category of a corresponding neuron N2 in the output layer L2.

Even when using the kind of anomaly in the categories, the categories may be assigned to only the known kinds of anomalies. If an amount of characteristics (check data) obtained from a test object X belongs to one of the categories assigned to the known kinds of anomalies, the test object X can be determined to belong to the corresponding abnormal category. Further, if an amount of characteristics does not belong to either a normal category or a known abnormal category, it is determined to be an unknown anomaly. As for the unknown anomalies, an anomaly identified from an actual test object X can be stored in connection with an amount of characteristics obtained therefrom in the training sample storage 10c. Then, when the collected number of data sets for the anomaly of one kind reaches a predetermined number (for example, 150) such data sets can be used as the training samples.

Second Embodiment

Figure 4:
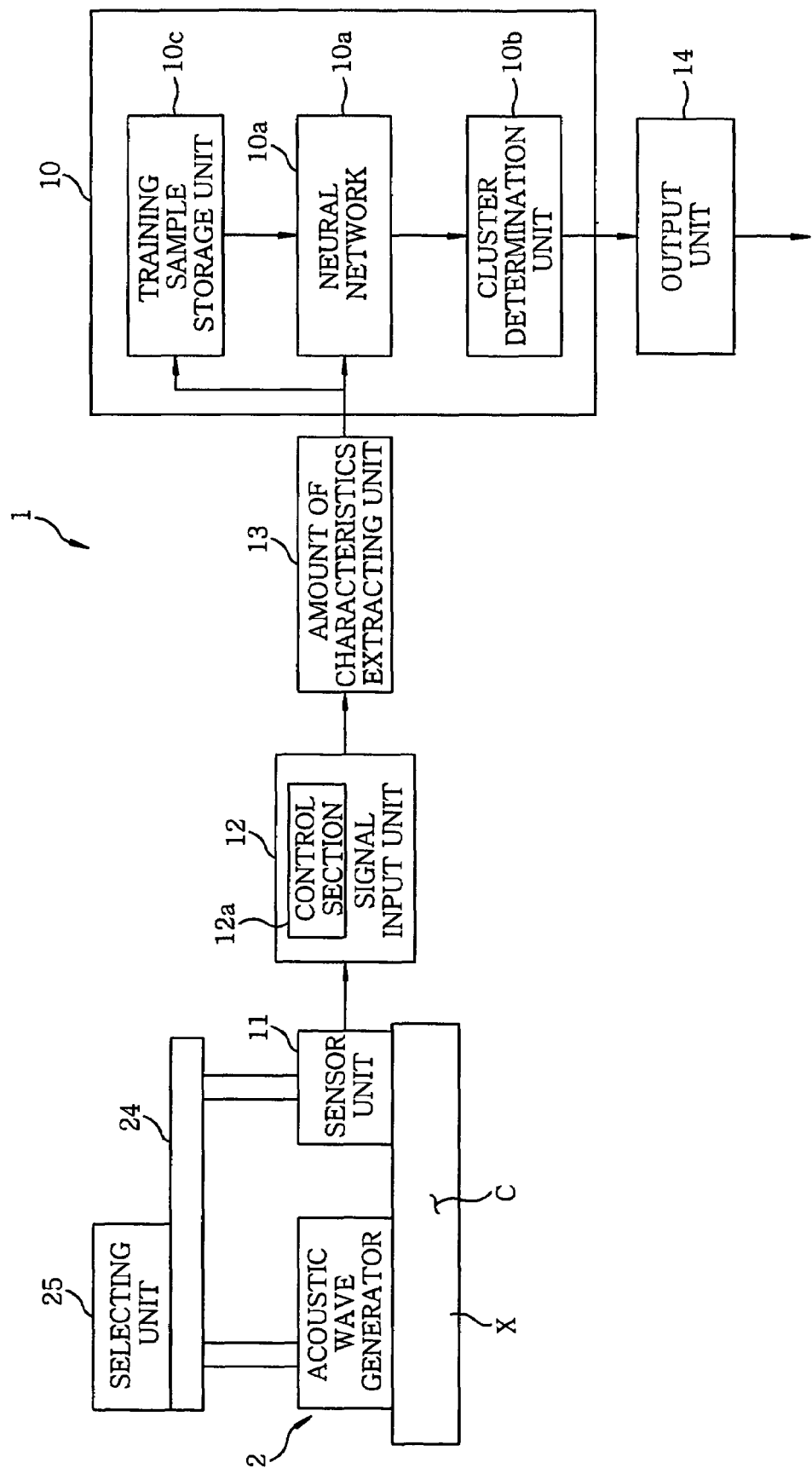
FIG. 4 is a block diagram illustrating a nondestructive inspection apparatus in accordance with a second embodiment of the present invention.

In the first embodiment, the vibration generator 2 was employed in impacting the test object X. However, as shown in FIG. 4, an acoustic wave generator for imparting vibrations to the test object X by an acoustic wave may be used as the vibration generator 2. Here, acoustic wave may not be within an audible frequency band but may have a frequency band higher or lower than the audible frequency band. In case of using the lower frequency, the acoustic wave generator employed in the vibration generator 2 virtually functions to impart actual vibrations to the test object X. The waveform, frequency, and duration of acoustic wave emitted by vibration generator 2 can be properly selected.

The waveform may be e.g., a sine wave, a rectangular wave, a triangular wave, or a sawtooth wave, and the frequency may be constant or may be stepwisely changed for example. As for the duration, the acoustic wave can be generated, e.g., continuously or only for a very short time to be considered as an impulse (hereinafter, referred to as an impulse type acoustic wave), or for a time longer than the impulse (hereinafter, referred to as a pulse type acoustic wave). The selection of the waveform, frequency and duration can be made by manipulating a selecting unit 25 provided in the vibration generator 2.

Since information about an impulse response or a step response can be obtained when using the impulse type acoustic wave or the pulse type acoustic wave, it is preferred to use, as an amount of characteristics, the time series of the effective values of power obtained from the respective unit periods Tu of the gate period Tg as described in the first embodiment.

In a case of transmitting the impulse type acoustic wave or the pulse type acoustic wave as the vibrations to the test object X, the starting point and the ending point of the gate period Tg can be set based on a moment when the acoustic wave is generated. In a case of continuously generating the acoustic wave, the starting point of the gate period Tg is set to, for example, a moment when a user presses a manipulation button (not shown).

When the waveform or frequency of the acoustic waves is changed, variations of the acoustic waves can be detected due to reflection, absorption, or the like in the test object X. Thus, it is possible to estimate the presence and the kind of an anomaly in the test object X and further it is also possible to attain information regarding the detailed internal structure of the test object X. However, enabling to attain detailed estimation requires substantial time to train, thus the choice of the acoustic waves and the kinds of the categories are properly set depending on available time for training and kinds of information required to be obtained from the inside of the test object X.

Moreover, as described in the first embodiment, the training samples can be collected even during the checking mode. Therefore, it may be preferable to start first using the nondestructive inspection apparatus in examining test objects after training the neural network with a relatively small number of categories, and then increase the number of classifiable categories by performing additional training after collecting training samples of further categories. Other structure and operation are identical to those of the first embodiment.

While the invention has been shown and described with respect to the embodiments, it will be understood by those skilled in the art that various changes and modification may be made without departing from the scope of the invention as defined in the following claims.

What is claimed is:

1. A nondestructive inspection apparatus comprising:
 a sensor unit for detecting vibrations transmitted through a test object from a vibration generator;
 a signal input unit for extracting a target signal from an electric signal outputted from the sensor unit;
 an amount of characteristics extracting unit for extracting multiple frequency components from the target signal as an amount of characteristics; and
 a decision unit having a competitive learning neural network for determining whether the amount of the characteristics belongs to a category, wherein the competitive learning neural network has been trained by using training samples belonging to the category representing an internal state of the test object,
 wherein distributions of membership degrees of the training samples are set in the decision unit, the distributions being set with respect to neurons excited by the training samples based on samples and weight vectors of the excited neurons, and
 wherein the decision unit determines that the amount of characteristics belongs to the category, if one of the excited neurons is excited by the amount of characteristics and the distance between the amount of characteristics and a weight vector each of one or more of the excited neurons, corresponds to a membership degree equal to or higher than a threshold determined by the distributions.

2. The nondestructive inspection apparatus of claim 1, wherein the distributions of the membership degrees are Gaussian distributions each being defined by a mean and a variance, and
 wherein variances of the Gaussian distributions are determined by distances between the training samples and weight vectors of the excited neurons and means of the Gaussian distributions are weight vector of the excited neurons.

3. The nondestructive inspection apparatus of claim 1 or 2, wherein the vibration generator includes a hammer to transmit vibrations to the inside of the test object by impacting same.

4. The nondestructive inspection apparatus of claim 1 or 2, wherein the vibration generator includes an acoustic wave generator to generate acoustic waves as the vibrations.

* * * * *